(12) United States Patent
Brasen et al.

(10) Patent No.: US 7,693,324 B2
(45) Date of Patent: Apr. 6, 2010

(54) OPTICAL SURFACE INSPECTION

(75) Inventors: Gernot Brasen, Mainz (DE); Christian Laue, Mainz (DE); Matthias Loeffler, Eisenberg (DE); Heiko Theuer, Mainz (DE)

(73) Assignee: International Business Machines Corporation, Armonk, NY (US)

( * ) Notice: Subject to any disclaimer, the term of this patent is extended or adjusted under 35 U.S.C. 154(b) by 731 days.

(21) Appl. No.: 11/160,707

(22) Filed: Jul. 6, 2005

(65) Prior Publication Data

US 2007/0009148 A1  Jan. 11, 2007

(30) Foreign Application Priority Data

Jul. 13, 2004 (EP) .................... 04103350

(51) Int. Cl.
*G06K 9/00* (2006.01)
(52) U.S. Cl. ............... 382/149; 382/141; 382/144; 382/145; 382/181
(58) Field of Classification Search ........ 382/141, 382/144, 145, 149, 181
See application file for complete search history.

(56) References Cited

U.S. PATENT DOCUMENTS

| | | | | |
|---|---|---|---|---|
| 6,011,874 A * | 1/2000 | Gluckstad | ............... | 382/276 |
| 6,064,484 A * | 5/2000 | Kobayashi et al. | .......... | 356/390 |
| 6,366,688 B1 | 4/2002 | Jun et al. | | |
| 6,608,690 B2 * | 8/2003 | Niu et al. | ............... | 356/635 |
| 7,015,467 B2 * | 3/2006 | Maldonado et al. | ......... | 250/306 |
| 2002/0012118 A1 | 1/2002 | Worster et al. | | |
| 2002/0154303 A1 | 10/2002 | Maeda et al. | | |
| 2002/0171051 A1 | 11/2002 | Nakagaki et al. | | |
| 2003/0058435 A1 | 3/2003 | Honda et al. | | |
| 2003/0076989 A1 | 4/2003 | Maayah et al. | | |
| 2003/0174877 A1 * | 9/2003 | Aiger | ............... | 382/145 |
| 2003/0203520 A1 | 10/2003 | Worster et al. | | |
| 2004/0022429 A1 | 2/2004 | Suzuki et al. | | |
| 2004/0037468 A1 | 2/2004 | Morishima et al. | | |
| 2004/0120579 A1 | 6/2004 | Cemic et al. | | |
| 2004/0126909 A1 | 7/2004 | Obara et al. | | |

FOREIGN PATENT DOCUMENTS

JP   11312716   11/1999
JP   2001056306  2/2001

* cited by examiner

*Primary Examiner*—Bhavesh M Mehta
*Assistant Examiner*—Michael Vanchy, Jr.
(74) *Attorney, Agent, or Firm*—Lisa U. Jaklitsch; Greenblum & Bernstein P.L.C.

(57) ABSTRACT

The present invention provides a method, an optical inspection apparatus as well as a computer program product for optical inspection of a surface. The optical inspection apparatus can be effectively applied for optical inspection of periodic structures on e.g. a semi-conductor wafer for the purpose of quality control. By effectively splitting a light beam into a plurality of spatially separated light beams and by selective usage of these light beams, various surface segments of the surface can be inspected simultaneously by superposition of respective images. A resulting superposition image can then be compared with a reference image for detection of defects of the surface.

22 Claims, 7 Drawing Sheets

OPTICAL SURFACE INSPECTION

TECHNICAL FIELD

The present invention relates to the field of optical inspection of a surface for detecting defects of the surface.

DESCRIPTION OF THE PRIOR ART

The control of quality is an important step in the manufacturing process of structured substrates, as e.g. semi-conductor wafers. Typically, semi-conductor wafers provide a grid or an array of periodic structures, each of which representing an integrated circuit or a chip. Since nowadays, semi-conductor wafers are predominantly subject to mass production, a subsequent quality control has to provide a throughput or inspection capacity that corresponds to the mass production process. For quality control of surfaces, like structured substrates, optical inspection techniques are a predestinated means. In principle, optical inspection techniques provide a fast, reliable and intuitive approach to the detection of surface defects of e.g. a structured substrate.

Generally, optical surface inspection can be performed in a plurality of different ways. For example, an operator manually and visually inspects the surface of a semi-conductor wafer by making use of a microscope. Obviously, this is rather cumbersome, time intensive as well as error prone. Also, when a semi-conductor wafer has a plurality of periodic structures, as e.g. a plurality of regularly arranged chips, each one of these periodic structures has to be manually inspected sequentially. Hence, the operator has to inspect every single periodic structure that is located on the semi-conductor wafer.

More sophisticated approaches may make use of signal processing means in order to acquire single images of various periodic structures of the semi-conductor wafer and to subsequently automatically compare the acquired images mutually or with a reference image. However, acquisition as well as comparison of various images of periodic structures typically requires sequential acquisition of single images. Sequential image acquisition is typically performed by acquiring a first image of a first chip, laterally displacing the semi-conductor wafer with respect to the optical inspection means and then acquiring a second image of a second chip of the semi-conductor wafer that has moved to an image acquisition area of the optical inspection means by the lateral displacement.

Even though surface inspection may reach a high degree of automation, a successive displacement of the semi-conductor wafer for acquisition of single images is still rather time intensive and may still not fulfill the stringent requirements of inspection throughput within a mass production process. On the one hand acquisition of a single image of a chip of the semi-conductor wafer takes at least a predefined exposure time and on the other hand the successive lateral displacement between optical inspection means and the semi-conductor wafer requires an additional translation time interval.

For example, referring to an optical surface inspection of a semi-conductor wafer featuring a grid of n×m single chips. The time needed for acquisition of the single images calculates approximately to n×m multiplied by the sum of image acquisition time for each single chip and the translation time interval needed for each lateral displacement.

A reduction of the inspection time and hence improving of inspection throughput may be realized by simultaneously imaging a plurality of chips of the semi-conductor wafer. However, an enlarging of a field of view, hence increasing of an inspection area, of an optical inspection system can only be realized at the expense of resolution decrease. For example, making use of a charge coupled device (CCD) based detector, only a limited amount of imaging pixels can be detected. An increase of the field of view therefore inevitably comes along with a decrease in resolution that might no longer guarantee a sufficient quality control.

Alternatively, a rather fast optical inspection of a wafer surface with respect of defects can generally be realized by means of a laser scanner detecting differences in the scattered light between subsequent structures on the wafer. However, laser scanning usually does not provide an optical image of the inspected structures nor does it allow sophisticated defect classification.

The present invention aims to overcome the described disadvantages by providing a method and an apparatus for optical surface inspection that allows for a fast and high resolution surface inspection of e.g. semi-conductor wafer surfaces.

SUMMARY OF THE INVENTION

The present invention provides a method of optical inspection of a surface that comprises acquisition of at least a first and second image of at least respective first and second segments of the surface. The acquired images are superimposed in order to form a superposition image and the superposition image is finally compared with a reference image in order to detect a defect of the surface. By superposition of the acquired images, a plurality of images, each of which having a high resolution, can be compared simultaneously with the reference image.

Preferably, each image is acquired with a maximum resolution that might only be limited by the resolution of the detector, like e.g. the number of pixels of a CCD chip. In particular, by superposition of a plurality of high resolution images, a single comparison of the resulting superposition image with a reference image provides sufficient information in order to determine whether any of the acquired and superimposed images is indicative of a defect of a corresponding segment of the surface.

Acquisition of the at least first and second images does preferably not involve any kind of positioning or displacing of either the surface or the optical inspection means. Principally, the inventive method allows to select a set of segments of the surface that shall become subject to optical inspection on the basis of a respective set of images.

According to a further preferred embodiment of the invention, the at least first and second images are acquired simultaneously or in partially overlapping time intervals. This allows for a remarkable decrease of optical inspection time by simultaneously maintaining a required resolution. Simultaneous acquisition of the at least first and the at least second images may also be realized by superimposing respective first and second optical fields before the image acquisition takes place. In this way the superposition step can be implemented all optically by superimposing of the at least first and second optical fields providing first and second images of respective surface segments.

According to a further preferred embodiment of the invention, the at least first and second segments comprise a size that corresponds to the size of a periodic structure of the surface. In this way each one of the at least first and second images provides a visual image of a segment of the surface that corresponds to a defined periodic structure of the surface. For example, when the surface comprises a semi-conductor wafer featuring a grid or an array of chips, each one of the at least first and second images provides a visual image of a particular chip of the semi-conductor wafer.

Ideally, the various chips, hence the periodic structures of the semi-conductor wafers are identical. By superimposing a set of images, each of which representing an identical periodic structure, deviations that occur in a single image due to a surface defect are still observable in the resulting superposition image. Especially by comparing the superposition image with a reference image and making use of further image manipulation means, like enhancing contrast of a comparison image, a defect in any image of the set of superimposed images can be sufficiently detected. Therefore, the field of view of each one of the at least first and second images, hence the size of respective first and second segments of the surface, are designed to match the periodicity of a semiconductor wafer.

The inventive method is by no means restricted to optical inspection of structured surfaces. Moreover, it can be universally applied to non structured, hence homogenous, surfaces that might later become subject to a structuring.

According to a further preferred embodiment of the invention, the method further comprises in response to the detection of a defect, performing of an examination procedure in order to identify one of the at least first and second segments having the defect. As described above, the inventive method of superposition and acquisition of a set of images of a set of segments of the surface, only allows to detect a defect that is located in a set of segments of the surface. So far the inventive method lacks detection of a particular segment featuring a detected defect.

The successive examination procedure provides an efficient approach to detect a particular segment of the surface that has a defect when the existence of a defect in a set of segments has been previously detected.

According to a further preferred embodiment of the invention, the examination procedure comprises the steps of sequentially acquiring at least one subset of the at least first and second images and then separately comparing the subset with the reference image in order to identify the subset that has the defect. Subsets may comprise an entire row or column of images that correspond to a respective row or column of surface segments. In this way, the entire surface can be inspected row and/or column wise in order to determine an occurrence of a defect. A grid of periodic structures may also be optically inspected row-wise and subsequently columnwise. Storing and comparing respective superposition images of rows and columns also represents an efficient way to find a particular segment of the surface featuring a defect. With respect to row wise inspection procedure, the time needed for inspecting of the entire surface can be reduced by a factor that is equivalent to the number of segments of a row.

Additionally, in order to retrieve a particular segment featuring a defect various other simultaneous and sequential detection schemes are universally applicable. For example, after identification of the subset that features the defect, a sub subset of the subset may become subject to an iterative application of the examination procedure.

Such an alternative examination procedure may continue until a selected subset only corresponds to a single image of a segment of the surface. For example, n×m periodic structures are arranged in a grid of n columns and m rows on a semiconductor wafer. The surface inspection may then be based on simultaneous acquisition and superposition of images representing an entire row of segments. In this way n single images are superimposed and simultaneously compared with the reference image.

By repeatedly performing this acquisition and comparison step for each row, hence m times the inventive method provides sufficient and reliable information of row-wise occurrence of defects. For example, only the superposition image of the n images of the first row is indicative of a defect. Then, in order to determine a particular segment having the defect, it is only logical to apply the subsequent examination procedure exclusively to the first row of the grid.

For example, a subset of the n images of the first row might be selected and corresponding images of this subset may become subject to simultaneous acquisition and superposition for defect detection purpose. When the defect is also present in the subset of acquired images, another subset of the subset can be determined and may become subject to a corresponding examination procedure. In the other case, when the defect is no longer present in the selected subset, a complementing subset may be selected that becomes subject to the examination procedure.

Other approaches for implementing the examination procedure are also conceivable. For example, in response to detecting a defect in a particular row, the single images of this particular row may become subject to subsequent image acquisition and image comparison steps.

Depending on the arrangement of the periodic structures, the size of the periodic structures as well as the number of periodic structures, a particular examination procedure of a plurality of examination procedures might be selected in order to provide the fastest and most reliable surface defect detection scheme.

According to a further preferred embodiment of the invention, comparison of the reference image with the superposition image and/or comparison of the reference image with any one of the at least first and second images is performed on the basis of image processing means. In particular, image processing means may refer to digital signal processing that can be performed by means of a computer with a corresponding software. For example, the superposition image can be subtracted from the reference image for visualizing deviations between the superposition image and the reference image. Subtracting of reference and superposition image may result in a comparison image that reflects defects in the segments of the surface.

Moreover, the image processing means may further be adapted to apply image manipulation procedures on either the superposition image, the reference image or the comparison image. In particular, by enhancing contrast of the comparison image, detection of defects is facilitated.

In another aspect, the invention provides an optical inspection apparatus for detecting a defect of a surface. The optical inspection apparatus comprises acquisition means for acquisition of at least a first image of an at least first segment of the surface and for acquisition of at least a second image of an at least second segment of the surface. The inspection apparatus further comprises superposition means for generating a superposition image by superimposing the first and the second images and further comprises image processing means for comparing the superposition image with a reference image in order to detect the defect of the surface.

According to a further preferred embodiment of the invention, the acquisition means comprise a detector for acquiring at least a first optical field and at least a second optical field. The first and second optical fields correspond to the at least first and second images. Typically, the detector is implemented as a CCD camera that allows for subsequent digital signal processing.

The optical inspection apparatus further comprises imaging means for imaging of the at least first and second images of the at least first and second segments onto the detector and further comprises a configurable spatial light modulator (SLM) for selecting the at least first and second optical fields by providing transmission of the at least first and second optical fields.

The imaging means can be implemented as an imaging lens or several imaging lenses in combination with other optical components, such as beam splitters and/or mirrors. Preferably, the imaging means provide a suitable imaging of the single periodic structures of the surface onto the detector. Hence, the imaging means provide sufficient adaptation of the optical inspection system to a given semi-conductor wafer. For example, the imaging means provide a focusing mechanism in order to generate a sufficiently focused and sharpened image on the detector.

The configurable spatial light modulator preferably provides a configurable transmission matrix for a plurality of optical fields representing a respective plurality of images of segments of the surface. In this way various segments of the surface can be selected for optical inspection by blocking all optical fields that do not correspond to the selected segment. Therefore, the plurality of optical fields representing the plurality of images of segments have to be spatially separated.

According to a further preferred embodiment of the invention, the superposition means comprise a diffractive optical element. Such a diffractive optical element effectively allows to combine a plurality of optical fields into a superimposed optical field.

Usage of a diffractive optical element for superposition of a plurality of optical fields is an efficient approach to combine the various optical fields by making use of a single optical element. Diffractive optical elements can be individually designed and manufactured for dedicated applications. For example, diffractive optical elements can be implemented as computer generated holograms serving as a universal means for light beam shaping.

According to a further preferred embodiment of the invention, the diffractive optical element being further adapted to provide generation of the at least first and second optical fields on the basis of a light beam entering the diffractive optical element. In this way an optical beam emanating from a light source can be split into a number of separate light beams, each of which providing imaging of a particular segment of the surface. Therefore, by making use of the diffractive optical element, a plurality of spatially separated light beams can be easily generated. Generation of the plurality of spatially separated light beams in combination with a configurable spatial light modulator effectively allows to simultaneously perform imaging of a set of segments of the surface by means of a corresponding configuration of the spatial light modulator.

The optical inspection apparatus can be operated in either reflection or transmission geometry. In the reflection geometry a light beam generated by a light source can be split into a plurality of separated light beams by means of a diffractive optical element that are subsequently directed on a configurable spatial light modulator. The spatial light modulator (SLM) effectively provides a transmission matrix for the plurality of spatially separated optical beams and thereby allows that only selected segments of the surface become subject to imaging.

The light beams that are transmitted by the SLM are appropriately focused on the surface, e.g. by means of a dedicated objective, and the light reflected at the selected segments of the surface is repeatedly transmitted through the same SLM and they are subsequently combined by means of the diffractive optical element. Hence the configurable SLM and the diffractive optical element provide effective means for generating required spatially separated light beams, for selecting particular segments of the surface that shall become subject to imaging and for superimposing optical fields that correspond to the images of the selected surface segments.

According to a further preferred embodiment of the invention, the imaging means further comprise an array of at least first and second microlenses. Preferably, the array of microlenses is adapted to the diffractive optical element. For example, the diffractive optical element splits a light beam into an array of 5×5 spatially separated light beams. This array of light beams then passes through the configurable SLM and enters an appropriate array of microlenses. In this configuration, the array of microlenses provides sufficient imaging of each of the 25 separate light beams. Preferably, the optical inspection apparatus is provided with a whole set of microlens arrays and diffractive optical elements that allows to universally adapt the optical inspection apparatus to various geometries of periodic structures on various types of substrates that become subject to surface inspection.

In still another aspect, the invention provides a computer program product for an optical inspection apparatus for detecting a defect of a surface. The computer program product comprises computer program means that are adapted to configure a spatial light modulator for providing transmission of at least first and second optical fields that correspond to at least first and second images of at least first and second segments of the surface. The computer program means are further adapted to process a superposition image being acquired and provided by a detector. Further, the computer program means are adapted to compare the superposition image with a reference image.

According to a further preferred embodiment of the invention, the computer program means are adapted to perform an examination procedure in order to identify one of the at least first and second segments that have a defect.

BRIEF DESCRIPTION OF THE DRAWINGS

In the following, preferred embodiments of the invention will be described in greater detail by making reference to the drawings in which.

DESCRIPTION OF THE PREFERRED EMBODIMENT

Figure 1:
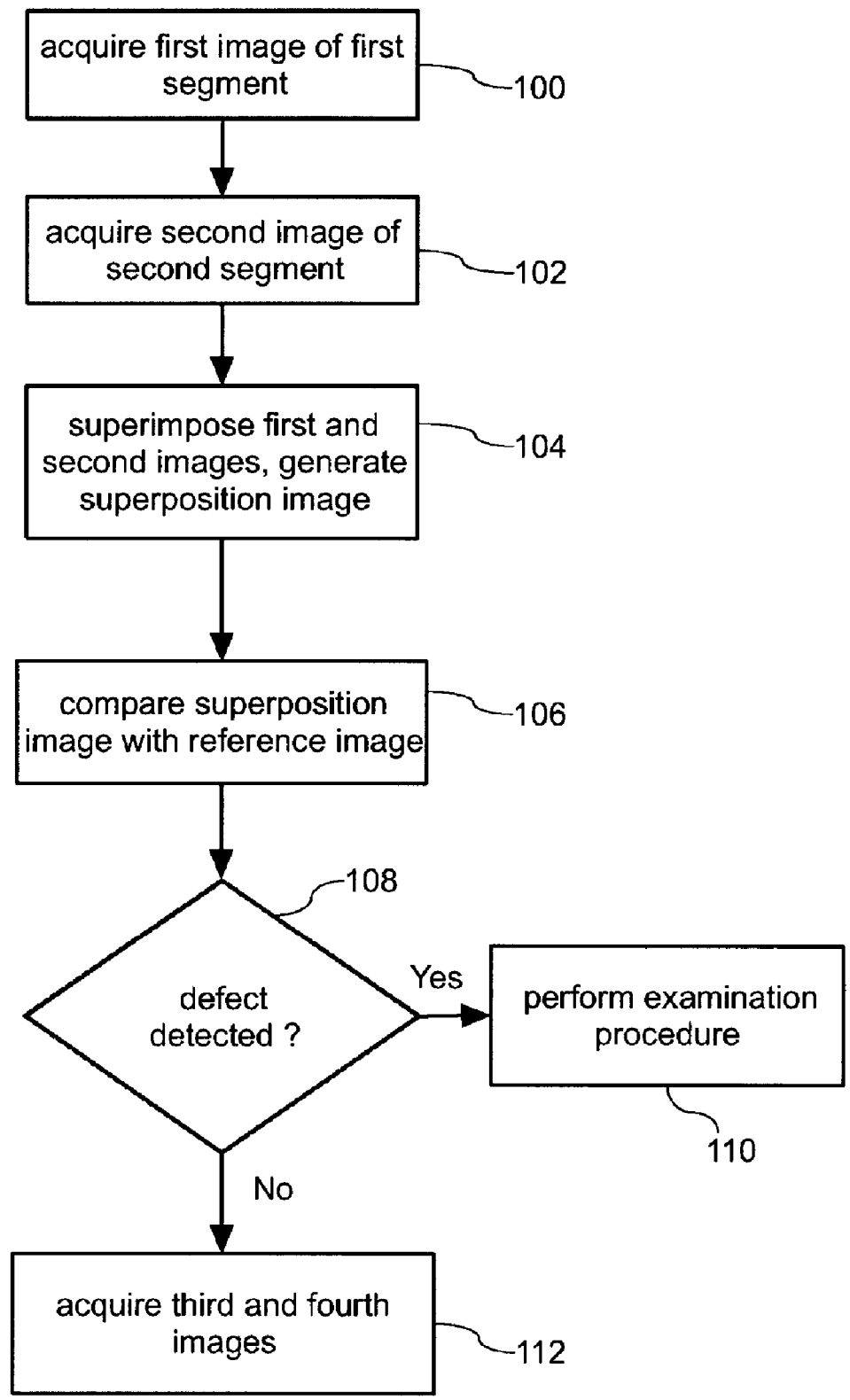
FIG. 1 illustrates a flow chart of acquiring, superimposing and comparing first and second images of respective surface segments.

FIG. 1 illustrates a flow chart for acquiring at least a first and a second image of respective first and second segments of the surface, to superimpose the first and second images for generating a superposition image and to compare the superposition image with a reference image in order to detect a surface defect. Therefore in a first step 100, a first image of the first segment is acquired. Thereafter in step 102, a second image of a second segment is acquired correspondingly. According to the invention, at least first and second images have to be acquired. Acquisition of images as well as superposition of images is by no means restricted to only two images. Moreover, the number of acquired and superimposed images may be adapted to required specifications of the surface inspection system.

In step 104 the acquired images are superimposed and a superposition image is generated thereof. Acquisition of images and their superposition are illustrated as sequential steps 100, 102, 104. Generally, the superposition of the images can be performed in any arbitrary way. For example a photographic film, i.e. a light sensitive medium, can be sequentially exposed with single images of various segments. Alternatively, every acquired image can be stored by e.g. digital signal processing means and can be accumulated to previously acquired and stored images.

Preferably, the superposition of various images is performed all optically even before image acquisition takes place. Principally, the superposition of the various optical fields, each of which representing an image of a particular surface segment, can be performed by means of an arrangement of mirrors and beam splitters. Moreover, superposition of the at least first and second images can be realized by making use of a diffractive optical element.

Especially by optically superimposing a plurality of optical fields, the superposition image can be acquired in a single acquisition step. In this way superposition of the plurality of images has not to be performed as a sequential step after acquisition of the images.

In step 106 the obtained superposition image is compared with a reference image. Comparison between the superposition image and the reference image can be based on digital signal processing means, hence computer supported image analysis. For example, a comparison image can be generated being indicative of deviations between the superposition image and the reference image. In particular when such a comparison image becomes subject to further image manipulation, like e.g. contrast enhancing, visibility of deviations between the superposition image and the reference image may be appreciably enhanced.

In a successive step 108, the result of the comparison is evaluated in order to determine whether a defect can be detected. When for example a contrast enhanced comparison signal is indicative of a defect, it is shown that at least one image of the at least first and second images has a defect. However, detection of a defect in the superposition image does not yet give any information which one of the superimposed images provides the defect.

Depending on the dedicated area of application of the inventive method, in response to a defect detection in step 108, a subsequent examination procedure can be performed in step 110 in order to identify at least one of the at least first and second segments that has the defect. Otherwise, when for example the method is only used in order to control whether a semi-conductor wafers is free of defects, the method may stop in response to a defect detection and classify the semi-conductor wafer, that is currently subject to the surface inspection, as scrap.

Alternatively, when in step 108 no defect of the surface has been detected, the method can continue with step 112 for acquiring subsequent at least third and fourth images. In principle, step 112 refers to a repeated application of the entire procedure for optical inspection of further surface segments.

Figure 2:
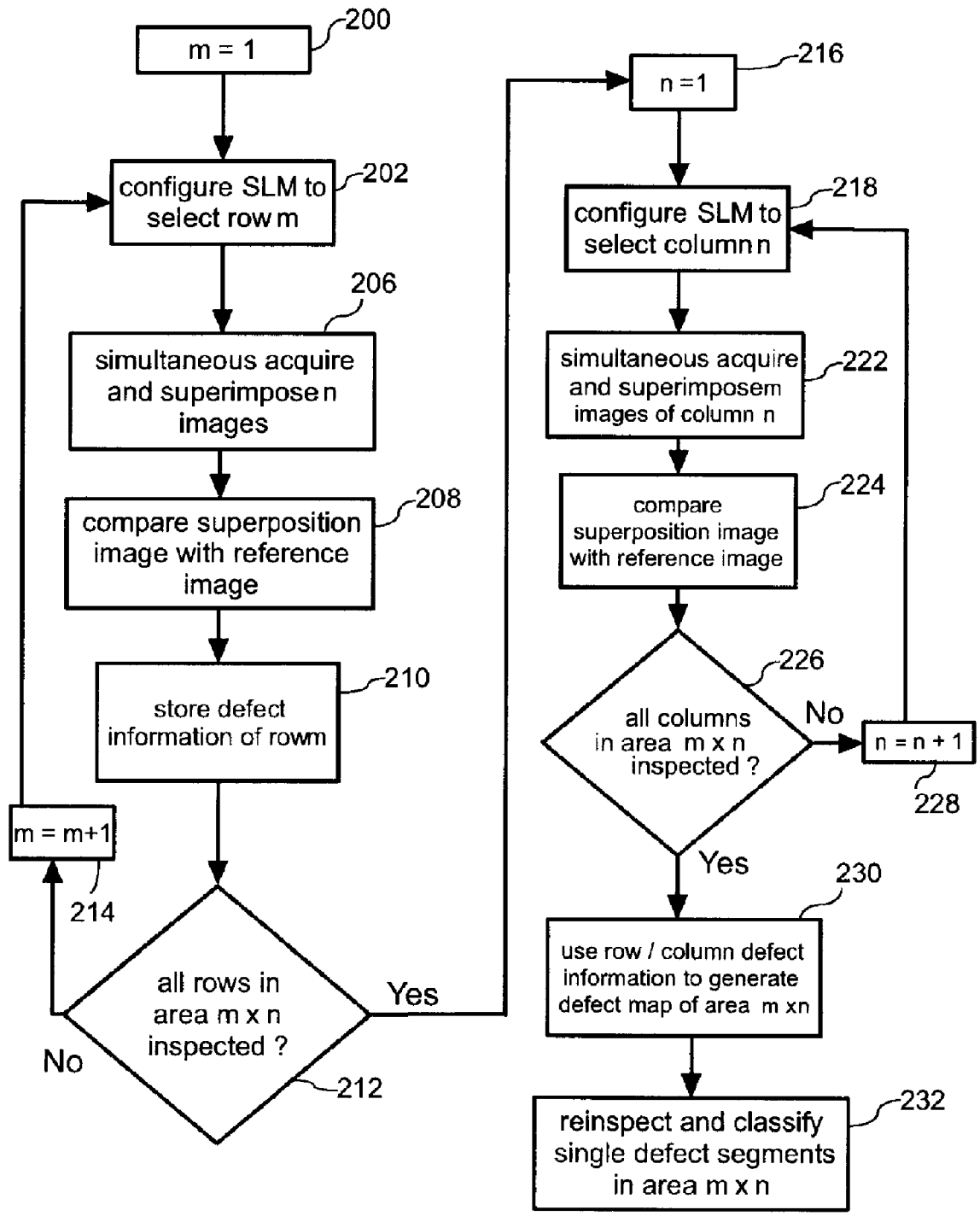
FIG. 2 illustrates a flow chart for detecting a defect in a superposition image and for subsequently identifying the segment having the defect.

FIG. 2 illustrates a flow chart for inspecting of a plurality of periodic structures that are arranged in an array of n columns and m rows on a substrate. In a first step 200 the row index m is initialized to 1. Thereafter, an appropriate configuration of the spatial light modulator is performed in step 202 in order to select a row with row index m. For this purpose corresponding segments of the spatial light modulator are switched to a transparent or non-transparent state. Consequently, only row m becomes subject to imaging. In principle, imaging can be performed in a reflection or transmission geometry depending on the properties of the substrate.

In the following step 206 an entire row m is simultaneously acquired and the corresponding n images are superimposed. It is irrespective for the present invention whether the single n images are simultaneously or sequentially acquired and whether superposition is performed prior or after acquisition of the images. However after execution of step 206, a superposition image is provided by superposition of all n images of row m.

Thereafter in step 208, the superposition image is compared with a reference image. This step 208 principally corresponds to the comparison step 106 of FIG. 1. In a successive step 210, any defect information that can be extracted from the comparison with the reference image is stored by making use of some storage device. In the successive step 212 it is determined whether all rows of the inspection area m.times.n have already been inspected. In case that not every row has been inspected yet, the method continues with step 214 where the row index m is incremented by 1. Thereafter the method returns to step 202 for configuring the SLM in order to select the next row m+1.

Given the case that all rows of the inspection area m×n have been inspected, then the method proceeds with step 216 after step 212. In step 216 the column index n is initiated to n=1. Thereafter, the method continues with step 218. In step 218 a the SLM is appropriately configured in order to select column n for surface inspection. Thereafter, in step 222 corresponding superimposed image of the selected column is acquired and thereafter in step 224 the acquired superposition image is compared with the reference image.

The comparison performed in step 224 may correspond to the comparison performed in step 208. Thereafter, in step 225 any defect information obtained by comparison of the superimposed column image with the reference image is stored by some kind of storage device. Thereafter, in step 226 it is checked, whether all columns n of the area m×n have already been subject to inspection. If there exists any column that has not yet been inspected, the method continues with step 228, where the column index n is increased by 1. After increasing the column index, the method returns to step 218 where the next column is effectively selected by appropriately configuring the SLM.

Otherwise when in step 226 it turns out, that every column of the area m×n has been subject to surface inspection, the method finally continues with step 230. There, the stored column and row defect information is analyzed in order to determine, which surface segments are erroneous. In particular, the row and column defect information can be correlated in order to determine a particular defect surface segment.

Optionally, after step 230, an additional step can be performed that triggers a re-inspection and classification procedure for segments that were determined to feature a defect.

Hence, the flow chart illustrated in FIG. 2 shows a procedure for sequentially checking entire rows and entire columns of an array of periodic structures. Compared to prior art solutions, where each surface segment has to be sequentially inspected thereby requiring at least an inspection time that equals n×m×acquisition time of a single image, the present invention provides a much faster approach to optical inspection of a surface. Given the case that a semi-conductor wafer does not have any defects, the inventive method provides optical inspection of the entire wafer by only sequentially acquiring m superposition images of the m rows of the array. Hence, by only inspecting the wafer row wise, it can be sufficiently determined whether there exists a defect or not. Depending on the result of such a row wise inspection procedure, an additional selective column wise inspection procedure may be applied.

Only in case an identification of defect segments is required, the inventive method will step wise inspect single columns of rows featuring a defect. Alternatively, the identification procedure performed by steps 218 through 228 can be further optimized by selecting a subset of columns of a row instead of selecting a single column of a row m.

Figure 3:
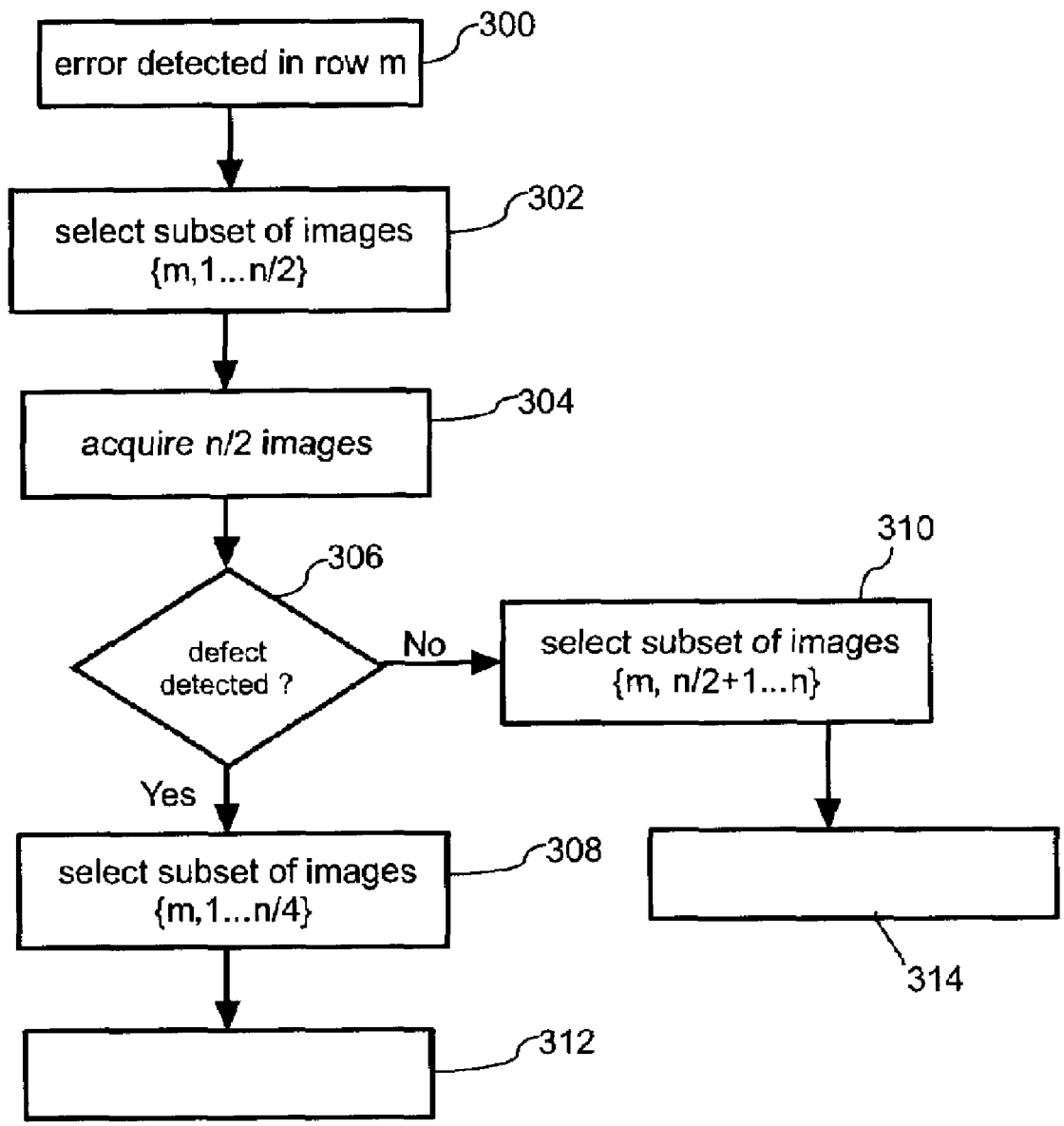
FIG. 3 illustrates a flow chart for performing a particular examination procedure for identifying a defect bearing segment, FIG. 4 schematically illustrates the optical inspection apparatus.

FIG. 3 is indicative of a flow chart for performing an examination procedure in order to identify a particular segment that has a defect. The first step 300 of FIG. 3 may follow step 210 of FIG. 2. Preferably, the examination procedure illustrated in FIG. 3 is performed in response to the detection of a defect in e.g. a row m. The purpose of the examination procedure is then to identify at least one particular segment of the n segments of row m that features a defect.

Therefore, in step 302 a subset of images is selected. For example the subset refers to the first half of the row m (m, 1 . . . n/2) after selection of the subset of images in step 302 in the next step 304, the selected subset of images is acquired and a corresponding superposition image is generated. Similarly as explained above the superposition image is exploited in order to detect a defect in any one of the selected images of the subset.

In step 306 it is checked whether the selected subset features any defect. If in step 306 a defect has been detected, the method will continue with step 308, where another subset of images will be selected. Preferably this subset is a subset of the already selected subset of images of step 302. For example, the first quarter of the n images of row m (m, 1 . . . n/4) are selected. Thereafter in step 312 a step corresponding to step 304 may be executed for acquisition of the images selected in step 308.

In the other case when in step 306 no defect has been detected, the method continues with step 310, where a complementary subset of images representing the second half of images of the n images of the row m is selected. Thereafter in step 314 the selected subset of step 310 is acquired, superimposed and analyzed.

Generally, the method illustrated in FIG. 3 may iteratively continue to select smaller subsets of images until a selected subset corresponds to a single image that features the defect. For example, when the row m has 16 images, one of which featuring a defect, optimized application of the method illustrated in FIG. 3 will retrieve the defect image by only 4 sequential acquisitions of subsets of images. In a corresponding way, the method may also be adapted for detecting of a plurality of defects that may occur in a single subset of images.

Figure 4:
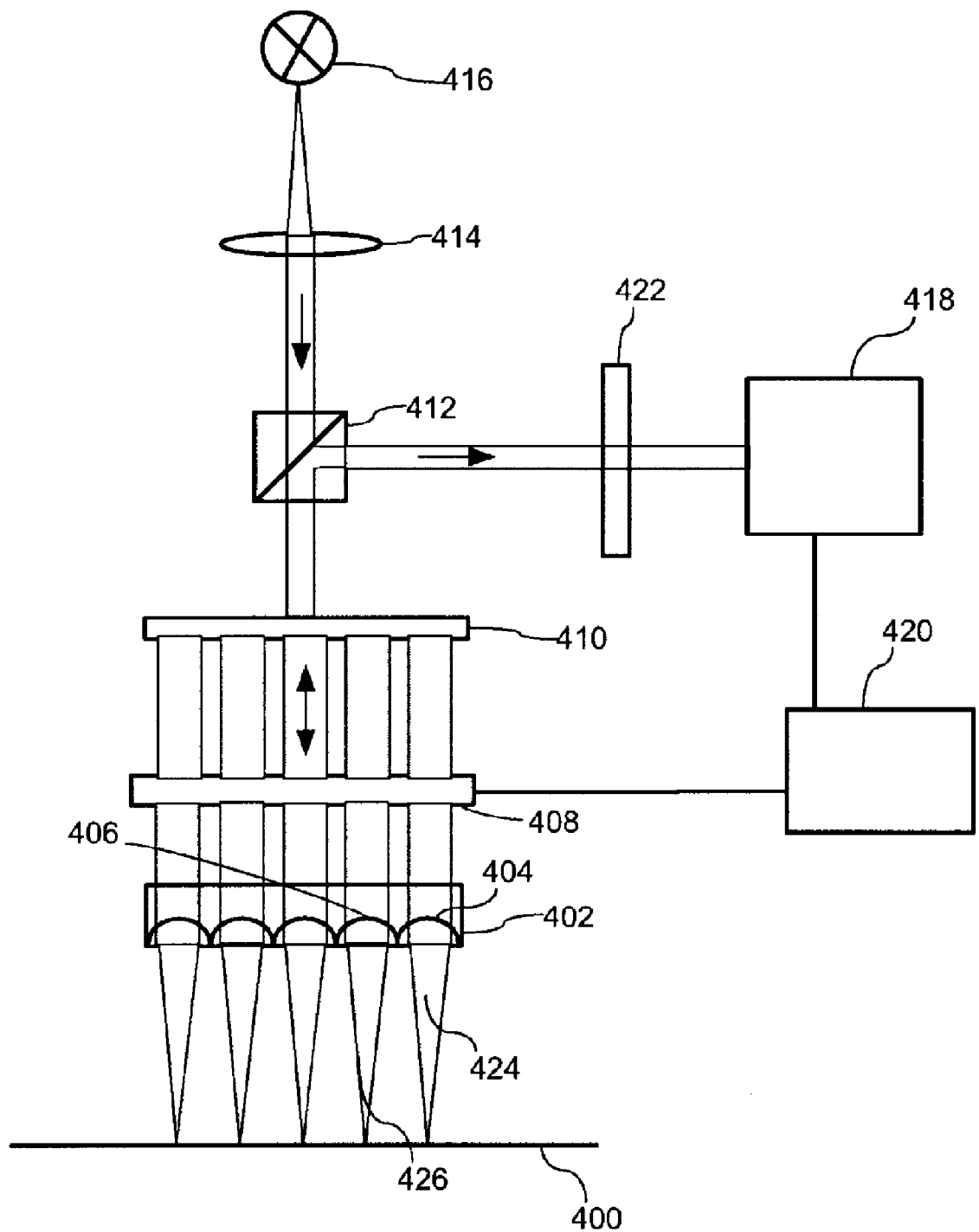

FIG. 4 schematically illustrates a preferred embodiment of the optical inspection apparatus. The optical inspection apparatus has a light source 416, a lens 414, a beam splitter 412, a diffractive optical element 410, a spatial light modulator (SLM) 408, a microlens array 402, an analyzer 422, a detector 418 as well as an image processor 420. The illustrated optical inspection apparatus is adapted for detecting defects of a surface 400.

In the illustrated embodiment the optical inspection apparatus is implemented in a reflection geometry, i.e. light generated by the light source 416 is directed to the surface 400 and reflected optical fields 424, 426 representing images of spatially separated segments of the surface 400 are detected by the detector 418 and become subject to image processing by means of the image processor 420.

Alternative inspection geometries like transmission geometry are requiring a transparent surface 400 can be implemented correspondingly.

A light beam emanating from the light source 416 is collimated by the lens 414 in order to provide a substantially non diverging light beam. This non diverging light beam propagates through the beam splitter 412 and hits the diffractive optical element 410. The diffractive optical element might be implemented as a computer generated hologram and features a specially fabricated phase shifting mask for the light beam. The light beam experiences diffraction at the diffractive optical element and thereby splits into regularly arranged spatially separated light beams.

The illustration of FIG. 4 is a side view and shows the splitting of the light beam into 5 separate light beams. Preferably, the splitting of the light beam occurs in the two dimensional transverse plane of the light beam and results in an array of 5×5=25 separate light beams. The spatially separated light beams are directed onto a spatial light modulator (SLM) 408 that is preferably implemented as a liquid crystal display or a liquid crystal based configurable matrix.

The SLM 408 provides transmission or blocking of selected light beams and thereby allows to selectively image particular segments of the surface 400. After transmission through the SLM 408, the remaining light beams enter the microlens array 402. The microlens array 402 preferably features as many microlenses as the diffractive optical element 410 generates spatially separated light beams. In this way each of the illustrated 5 light beams is separately directed by one microlens 404, 406 of the microlens array 402 towards 5 different segments of the surface 400.

Light 424, 426 reflecting from the surface 400 is appropriately imaged by the microlenses 404, 406 in order to produce a sharp image on the detector 418. The reflected light beams 424, 426 re-enter the spatial light modulator 408 that repeatedly provides transmission for the 5 illustrated light beams. Thereafter the light beams re-enter the diffractive optical element 410 resulting into a superposition, hence spatial Overlapping of the single reflected optical fields 424, 426. In this way, the diffractive optical element 410 effectively provides superposition of the various images.

By means of the beam splitter 412 the reflected and superimposed optical fields 424, 426 are reflected towards the detector 418. On their way to the detector 418 the reflected light 424, 426 passes the analyzer 422. The analyzer 422 is particularly relevant when the SLM 408 is implemented as a polarizing matrix as illustrated below in FIG. 5. In this case only by combining SLM 408 and analyzer 422, a required spatial transmission matrix for the optical beams can be generated. In principle, the analyzer 422 can be arbitrarily placed anywhere in the optical path. Preferably, the analyzer is an integrated part of the SLM.

The detector 418 is preferably implemented as a CCD camera and may further be controlled by an image processor 420 that in turn can be implemented as a personal computer for example. Moreover, the image processor not only serves to compare the superposition image acquired by the detector 418 with the reference image. Moreover, the image processor 420 may be adapted to configure the SLM for selection of particular images.

In this way the image processor 420 serves as a universal component of the optical inspection apparatus for providing digital signal processing of acquired images and for controlling the configurable component 408 of the optical inspection apparatus. Additionally, by means of the image processor 420, an interplay between image processing and selection of various images can be sufficiently controlled in order to perform predefined examination procedures.

Figure 5:
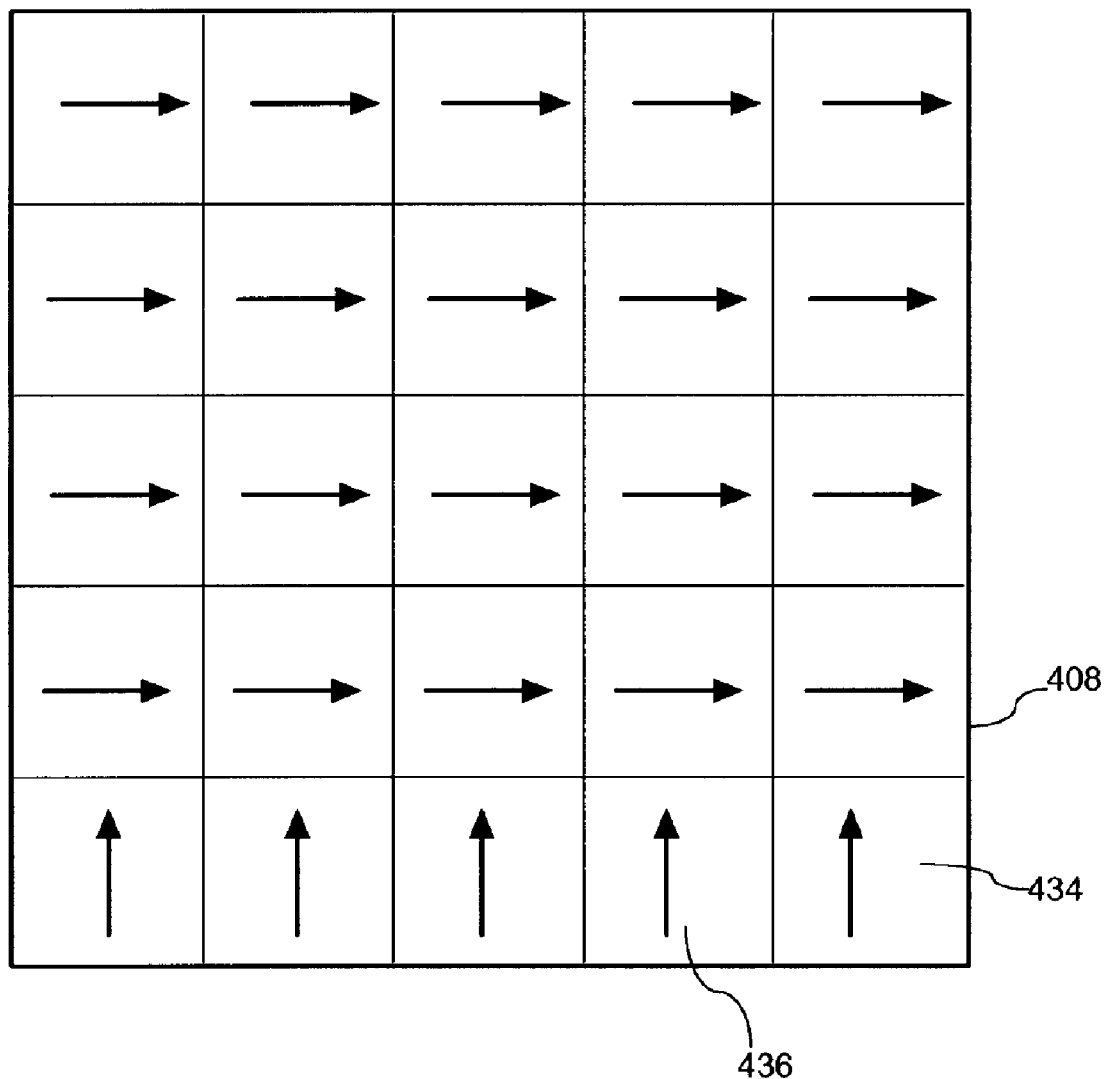
FIG. 5 shows the active aperture of the configurable spatial light modulator featuring segments with different polarization.

FIG. 5 is illustrative of a top view of the active aperture of the spatial light modulator 408. Here, the spatial light modulator is segmented in 5×5 segments, each of which being separately configurable as a linear polarizing element. The arrows in the modulator segments 434, 436 indicate the direction of polarization for maximum transmission. Maximum transmission implies that the analyzer 422 transmits optical signals featuring a polarization in the vertical direction.

Preferably, the analyzer 422 can be incorporated into the spatial light modulator. In this case the spatial light modulator 408 directly serves as a transmission matrix and in the configuration shown in FIG. 5 only the lower row of modulator segments 434, 436 will provide transmission of light. All other modulator segments featuring a horizontally aligned polarization are oriented at 90 degrees with respect to the analyzer 422. Consequently, the upper 4 rows serve to block 20 of the 25 spatially separated beams generated by the diffractive optical element 410.

Referring to FIG. 4 the reflected light 424 will be transmitted by modulator segment 434 and reflected light 426 will be reflected by modulator segment 436. Since the SLM 408 is configurable any one of the indicated modulator segments can change its polarization state. This allows for selective imaging of various segments of the surface 400.

Figure 6:
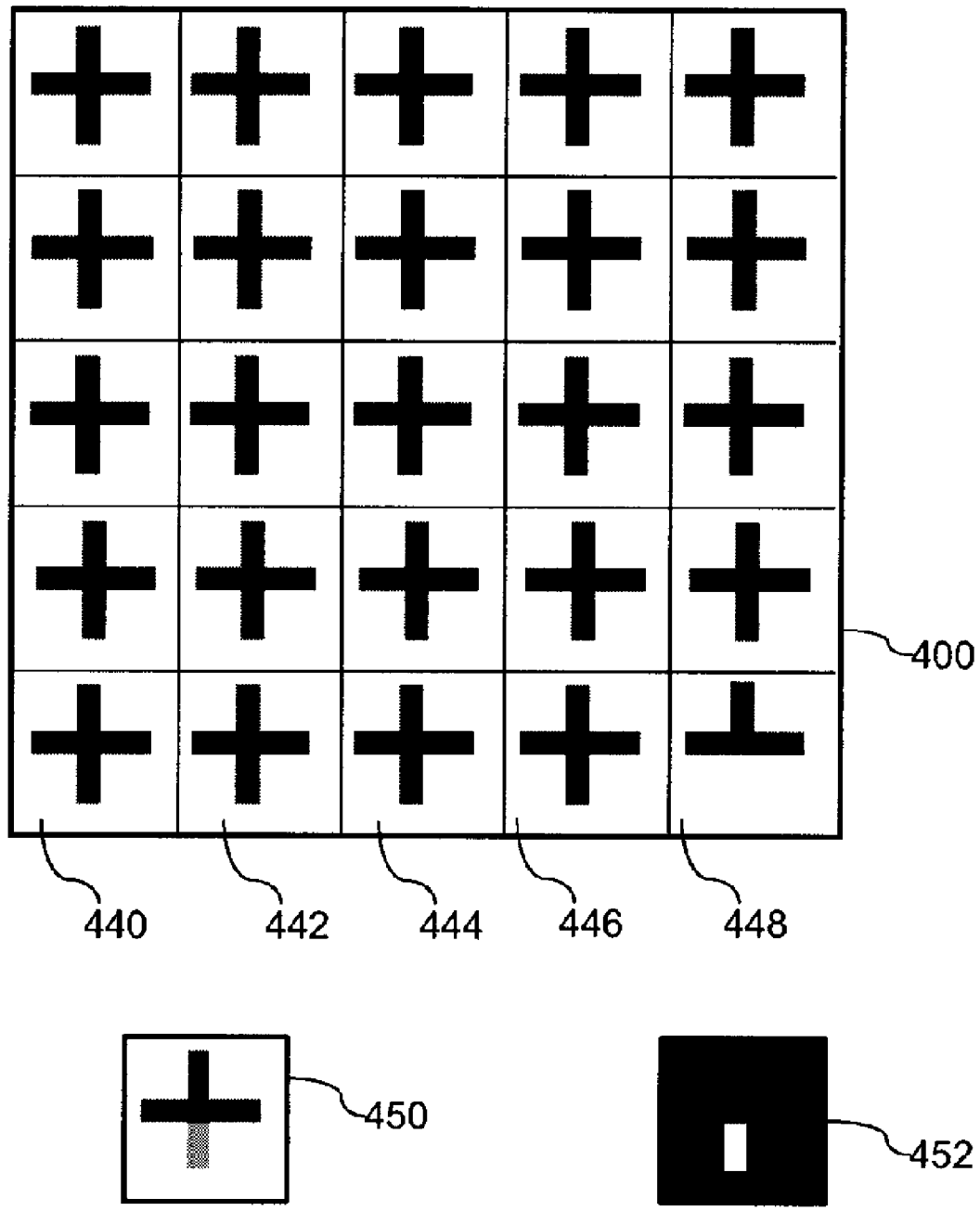
FIG. 6 shows a top view of a semi-conductor wafer, a superposition image and a comparison image, FIG. 7 schematically illustrates a beam combination unit for superposition of single images.

FIG. 6 illustrates a top view of e.g. a semi-conductor wafer featuring 25 periodic structures that are arranged in a 5×5 array. The periodic structures of the lower row 440, 442, 444, 446 are all identical but the structure in the lower right corner 448 clearly deviates from all other periodic structures and consequently features a defect.

Applying the inventive method on the surface 400 of the illustrated structured substrate by making use of a row-wise simultaneous optical inspection, a superposition image 450 can be generated that refers to the superposition of the surface segments 440 . . . 448 of the lower row. The defect of surface segment 448 reflects in a lower saturation in the superposition image 450. Subtracting the superposition image 450 from a reference image, like an image of surface segment 440 or a some other predefined and available reference image, a comparison image can be effectively generated. Enhancing contrast for example in combination with e.g. negating the comparison image may result in a contrast enhanced comparison image 452 that clearly shows the detected defect. Based on this single image acquisition, the inventive method provides reliable information that only the last row of surface segments has a defect.

Compared to a prior art solution where each one of the 25 surface segments has to be aligned and separately inspected, by applying the inventive method in a row wise modus only, 5 instead of 25 sequential image acquisition steps have to be performed in order to determine whether there exists a defect on the surface 400.

Remarkably, the inventive optical inspection is performed with the same resolution as a prior art implementation. Applying a subsequent column-wise optical inspection in combination with storing and correlating the acquired superposition images, distinct surface segments featuring defects can be sufficiently identified. In the latter case 10 superimposed images have to be acquired and analyzed.

Figure 7:
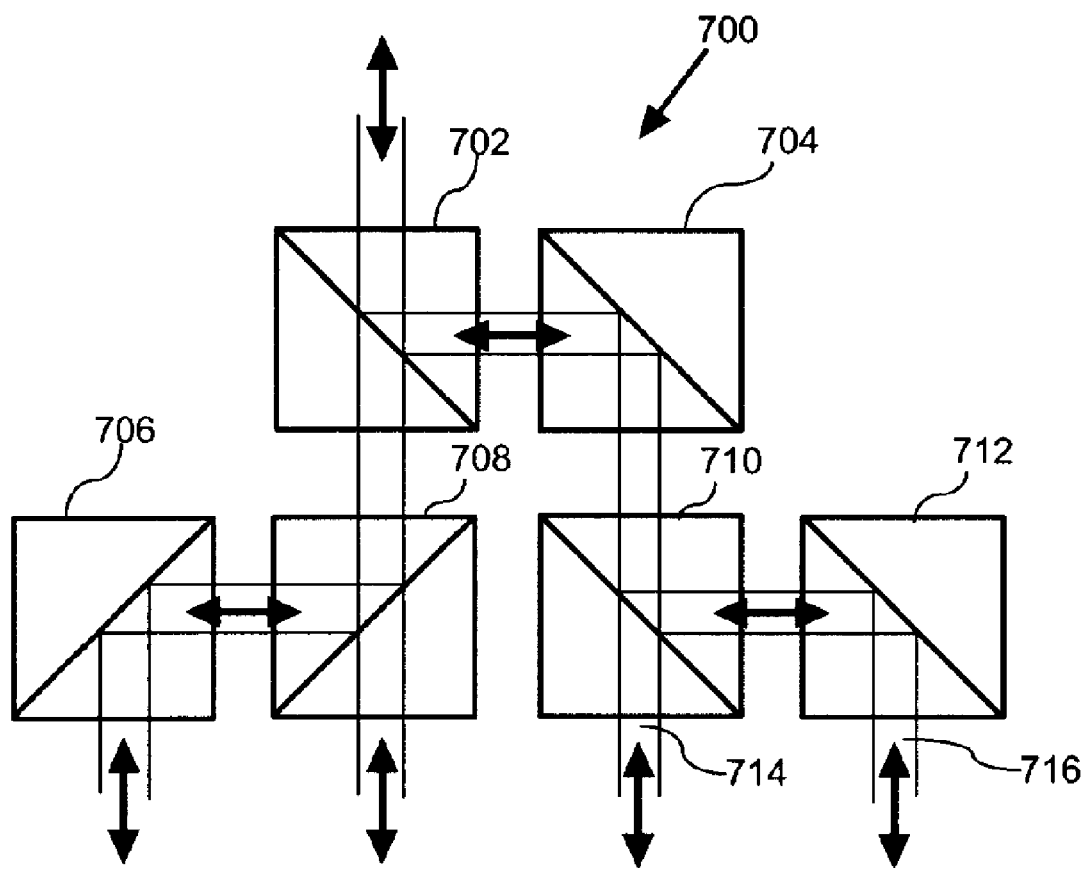

FIG. 7 schematically illustrated a basic embodiment of a beam combination unit 700 having six separate beam splitters. The six beam splitters 702, 704, 706, 708, 710 and 712 are arranged in such a way, that a light beam being incident on beam splitter 702 is split into four separate beams emanating from the beam combination unit 700. These four beams are in turn adapted to separately acquire an image of a respective surface segment. When reflected at the surface these single light beams 714, 716 are recombined by the arrangement of beam splitters to form the desired superposition image. Hence, the beam combination unit 700 serves to replace the diffractive optical element 410 that is illustrated in FIG. 4.

What is claimed is:

1. A method of optical inspection of a surface that is known to have a defect comprising the steps of:
    acquiring at least a first image of an at least first segment comprising a size of a periodic structure of the surface;
    acquiring at least a second image of an at least second segment comprising the size of the periodic structure of the surface;
    generating a superposition image by superimposing the first and the second images;
    comparing the superposition image with a reference image in order to detect a defect of the surface and, when no defect is found, iteratively selecting a complementary subset of images of the at least first and second segments to create a superposition image of the different selected subsets of images until it is determined that one of the selected subsets of images has the defect; and
    stopping the optical inspection when a defect is found.

2. The method according to claim 1, wherein the at least first and second images are acquired simultaneously or in partially overlapping time intervals.

3. The method according to claim 1, further comprising, in response to the detection of the defect, performing an examination procedure in order to identify one of the at least first and second segments having the defect.

4. The method according to claim 3, wherein the examination procedure comprises the steps of:
    sequentially acquiring at least one subset of the at least first and second images; and
    separately comparing the subset with the reference image in order to identify the subset having the defect.

5. The method according to claim 4, wherein comparison of the reference image with the superposition image and/or comparison of the reference image with any one of the at least first and second images is performed on the basis of image processing means.

6. An optical inspection apparatus for detecting a defect known to exist on a surface comprising:
    acquisition means for acquisition of at least a first image of an at least first segment comprising a size of a periodic structure of the surface and for acquisition of at least a second image of an at least second segment comprising the size of the periodic structure of the surface;
    superposition means for generating a superposition image by superimposing the first and the second images;
    image processing means for comparing the superposition image with a reference image in order to detect the defect of the surface prior to selecting other subsets and, when no defect is found, iteratively selecting a complementary subset of images of the at least first and second segments to create superposition image of the different selected subsets of images until it is determined that one of the selected subsets of images has the defect; and
    one or more means for:

determining whether all segments on the surface have been inspected, and if not, iteratively indexing to another segment on the surface for inspection; and stopping the optical inspection when a defect is found by the comparing the superposition image with a reference image.

7. The optical inspection apparatus according to claim 6, the acquisition means further comprising:
a detector for acquiring at least a first optical field and at least a second optical field, the first and second optical fields corresponding to the at least first and second images;
imaging means for imaging of the at least first and second images of the at least first and second segments onto the detector; and
a configurable spatial light modulator for selecting the at least first and second optical fields by providing transmission of the at least first and second optical fields.

8. The optical inspection apparatus according to claim 7, the superposition means comprising a diffractive optical element.

9. The optical inspection apparatus according to claim 8, wherein the diffractive optical element being further adapted to provide generation of the at least first and second optical fields on the basis of a light beam entering the diffractive optical element.

10. The optical inspection apparatus according to claim 9, wherein the imaging means further comprising an array of at least first and second microlenses.

11. A system for an optical inspection apparatus for detecting a defect known to exist on a surface comprising:
a means for configuring a spatial light modulator for providing transmission of at least first and second optical fields corresponding to at least first and second images of at least first and second segments of the surface, wherein the first segment comprises a size of a periodic structure of the surface and the second segment comprises the size of the periodic structure of the surface;
a means for receiving a superposition image of the at least first the second images acquired and provided by a detector; and
a means for comparing the superposition image with a reference image by subtracting the superposition image from the reference image prior to selecting other segments and, when no defect is found, begin iteratively selecting a complementary subset of images of the at least first and second segments to create a superposition image of the different selected subsets of images until it is determined that any of the selected subsets of images has the defect.

12. The system of claim 11, further comprising a means for performing an examination procedure in order to identify one of the at least first and second segments having the defect.

13. The method of claim 1, wherein the comparing includes creating a comparison image by subtracting the superposition image from the reference image.

14. The method of claim 13, further comprising negating the comparison image to show a detected defect.

15. The method of claim 6, wherein the comparing includes creating a comparison image by subtracting the superposition image from the reference image.

16. The method of claim 15, further comprising negating the comparison image to show a detected defect.

17. The system of claim 11, wherein the spatial light modulator blocks selected light beams thereby allowing particular segments of the surface to be selectively imaged.

18. The method of claim 1, further comprising determining whether all segments have been inspected, and if not, iteratively indexing to another segment for inspection.

19. The method of claim 18, further comprising triggering a reinspection and classification procedure for defects found on the surface and iteratively selecting smaller subsets on the surface where defects are found until the selected subset corresponds to a single image that features the defect.

20. The method of claim 19, further comprising triggering a reinspection and classification procedure for segments found to have a defect.

21. The method of claim 20, further comprising iteratively selecting smaller subsets of the images until the selected subset corresponds to a single image that features the defect.

22. The method of claim 21, further comprising extracting the defect and storing the defect in a storage device.

* * * * *